United States Patent [19]

Misato et al.

[11] 3,983,214

[45] Sept. 28, 1976

[54] FUNGICIDAL COMPOSITIONS AND METHOD FOR PROTECTING PLANTS BY THE USE THEREOF

[75] Inventors: Tomomasa Misato, Tokyo; Keng Tang Huang, Wako; Yasuo Homma, Kamifukuoka; Toshiro Shida, Kawasaki; Hachiro Wakamatsu, Musashino, all of Japan

[73] Assignee: Ajinomoto Co., Inc., Tokyo, Japan

[22] Filed: Feb. 12, 1975

[21] Appl. No.: 549,493

Related U.S. Application Data

[62] Division of Ser. No. 419,067, Nov. 26, 1973, abandoned.

[30] Foreign Application Priority Data

Dec. 8, 1972 Japan............................... 47-123654
Dec. 8, 1972 Japan............................... 47-123655
Feb. 28, 1973 Japan............................... 48-23251

[52] U.S. Cl.................................. 424/180; 424/199
[51] Int. Cl.²........................................ A01N 9/00
[58] Field of Search................................. 424/180

[56] References Cited
OTHER PUBLICATIONS

Borge et al., "*Antagonistic Effects . . . Inhibitory Lipid Factors,*" para. 1334a, p. 1348 – Chem. Abstracts, vol. 80, 1974.
Kneifel et al., "*Metabolic Products . . . Ex Foliatus,*" pp. 20–27. J. of Antibiotics, vol. 27, Jan. 1974.
Klyuchkin, V., "Effect of Moist Heat . . . Lipids", Chem. Abst., vol. 82, 1975, p. 56209, para. 56212f.

*Primary Examiner*—Lewis Gotts
*Assistant Examiner*—Cary Owens
*Attorney, Agent, or Firm*—Sherman & Shalloway

[57] ABSTRACT

Fungicidal compositions for agricultural and horticultural use which contain as an active ingredient one or more compounds selected from the group consisting of tartaric acid, oxalic acid, fumaric acid, citric acid, alkali metal salts of these organic acids, ferric citrate, ferric lactate, glycerine, aluminum chloride and esters formed between sugar and higher fatty acids having 8 to 18 carbon atoms. These compositions exhibit excellent protective effects against attack by plant disease fungi, bacteria or virus and have no phytotoxicity and no mammalian toxicity and present no risk of causing the pollution of soil, human, cattle and poultry. The protective effects of these active ingredients are greatly enhanced when they are applied to plants in combination with a phosphatide. And a method for protecting plants by the use thereof.

22 Claims, No Drawings

FUNGICIDAL COMPOSITIONS AND METHOD FOR PROTECTING PLANTS BY THE USE THEREOF

This is a division, of application Ser. No. 419,067, filed Nov. 26, 1973, and now abandoned.

The present invention relates to fungicidal compositions or agents which exhibit excellent fungicidal effects and in which there is no risk of pollution being caused thereby; and to a method for the use thereof. More particularly, the present invention relates to fungicidal compositions for agricultural and horticultural use which comprise or consist of fungicidal amounts of one or more compounds selected from the group consisting of tartaric acid, oxalic acid, fumaric acid, citric acid, alkali metal salts of these organic acids, ferric citrate, ferric lactate, glycerine, aluminum chloride and esters formed between sugar and higher fatty acids having 8 to 18 carbon atoms, and a carrier for agricultural and horticultural formulation.

The term "fungicidal composition or agent", as used herein and in the appended claims, is meant to include bactericidal, anti-virus compositions or agents in addition to its literal meaning.

Compounds of heavy metals such as copper, mercury and arsenic, as well as organophosphorus and organochlorine compounds have been used practically for the control of plant diseases, but these fungicides have in all cases not been completely satisfactory because of their pollution of soil, their strong phytotoxicity, residual toxicity in food crops, high mammalian toxicity or irritative effects on the human skin and eyes.

As a result of our extensive research for a compound which, while not possessing any of the foregoing faults as seen in the conventional fungicides, exhibits preventive effects against fungal plant diseases, we have now found that tartaric acid, oxalic acid, fumaric acid, citric acid, alkali metal salts of these four organic acids, ferric citrate, iron lactate, glycerine, aluminum chloride and sugar esters whose ester groups are esters of higher fatty acids having 8 to 18 carbon atoms exhibit excellent preventive effects against numerous plant diseases such as rice blast and rice leaf blight, which are the main diseases of the rice plant, citrus melanose, cucumber anthracnose, cucumber phytophthora rot, cucumber powdery mildew, cucumber downy mildew, tomato leaf mold, tomato late blight, tomato leaf spot, tabacco mosaic virus, cucumber green mottle mosaic virus and others, and that they have no phtotoxicity with extremely low mammalian toxicity, and that moreover there is no risk of causing the pollution of soil, plants, human beings, cattle and poultry.

As can be readily appreciated from the fact that all of the active ingredients in the present invention are widely used as additives for various foods and most of them occur in nature, they possess substantially no mammalian toxicity. Hence, the safety of the active ingredient of the invention fungicidal composition is exceedingly great, with the consequence that though it may be residually present in crops, the crops can be directly used as food for man or cattle and poultry feed, or after their simple washing. Thus it becomes possible to use the composition of this invention up to immediately before the harvesting period, the practice which has been avoided in the case of the conventional fungicidal compositions. It can be applied with especial convenience up to the time of harvesting of such plants as fruit-bearing plants, berry-bearing plants, vegetables and tobacco, including such as citrus, persimmon, apple, pear, peach, plum, apricot, cherry, loquat, grape, fig, pineapple, banana, strawberry, olive, tomato, eggplant, pepper, cucumber, melons, watermelon, pumpkin, radish, cabbage, cauliflower, turnip, onion, asparagus, lettuce, carrot, celery, spinach, dasheen, ginger, pea, potato, beans, rice, barley, wheat, etc.

The active ingredients of the present fungicidal composition are readily available in great quantities and at low cost. Furthermore, they are completely harmless to man, and domestic animals and fowls, and there is no need to exercise any special caution in their handling. Again, there is no possibility of their causing environmental pollution. Further, as previously noted, their application to crops right up to the time the crops are harvested can be carried out with complete safety.

As to the organic acids selected from the group consisting of tartaric acid, oxalic acid, fumaric acid and citric acid which are active ingredients in the present invention, they may also be employed in the form of their alkali metal salts such as sodium and potassium salts. As to sugar esters, they may be the esterified product of sugar and higher fatty acids having 8 to 18 carbon atoms, such as caprylic acid, lauric acid, palmitic acid and myristic acid. As used in the present specification and appended claims, the term "sugar" refers to sucrose; the term "sugar ester" means sucrose fatty acid ester.

Among the active ingredients of the present fungicidal composition, the following eleven compounds are especially preferred.

| No. | Compound |
| --- | --- |
| 1 | D-tartaric acid |
| 2 | DL-tartaric acid |
| 3 | Oxalic acid |
| 4 | Citric acid |
| 5 | Fumaric acid |
| 6 | Ferric citrate |
| 7 | Ferric lactate |
| 8 | Glycerine |
| 9 | Aluminum chloride |
| 10 | Sugar laurate |
| 11 | Sugar myristate |

The active ingredients of the present invention are especially useful in controlling the following fungi, bacteria and virus which tend to attack food crops: *Pyricularia orzae*, the causative organism of rice blast; *Xanthomonas oryzae*, the causative organism of bacterial leaf blight; *Xanthomonas citri*, the causative organism of citrus canker; *Colletotrichum lagenarium*, the causative organism of cucumber anthracnose; *Phytophthora parasitica*, the causative organism of cucumber phytophthora rot; *Sphaerotheca fuliginea*, the causative organism of cucumber powdery mildew; *Pseudoperonospora cubensis*, the causative organism of cucumber downy mildew; *Cladosporium fulvum*, the causative organism of tomato leaf mold; *Phytophthora infestans*, the causative organism of tomato late blight; *Alternaria tomato*, the causative organism of tomato leaf spot tabacco mosaic virus, the causation of tabacco mosaic; cucumber green mottle mosaic virus, the causation of cucumber green mottle mosaic, and others.

The active ingredients of the fungicides of the present invention may be directly applied to the fungus-susceptible plant surface, or it may be applied thereto in any formulation such as granules, dusts, emulsifiable concentrates, wettable powders, pastes, oil agents, aerosols, fogs or fumigants with suitable solid carriers, liquid carriers, emulsifying and dispersing agents and the like, as in the case of the usual formulations well known in the art. Examples of these carriers include clay, kaolin, bentonite, acidic terra abla, diatomaceous earth, calcium carbonate, nitrocellulose, starch, acacia, carbon dioxide, freon and the like. Also, the invention active ingredients may be suitably compounded with those auxiliary agents which are usually employed in the formulation of fungicides, e.g., surface active agents which serve as a spreading, dispersing and emulsifying agent. Examples of such surface active agents are soap, higher alcohol sulfates, alkyl sulfonates, alkylaryl sulfonates, quaternary ammonium salts, polyalkylene oxides and the like. The preferred concentration of the active ingredient in the fungicidal composition is about 0.1 – 90 % by weight. However, the concentration may be suitably varied in accordance with the intended use of the fungicide.

The amount of the fungicidal composition to be applied may be varied according to such factors as the formulation of the composition, the class of the active ingredient or the concentration of the active ingredient in the composition. It is usually applied at the rate of about 10 grams per 10 ares to 2000 grams per 10 ares, and preferably 50 grams per 10 ares to 1000 grams per 10 ares, calculated as the active ingredient. However, greater amounts may be applied, if desired.

The active ingredients of this invention may also be employed in admixture with herbicides, insecticides, other fungicides, soil conditioners, and fertilizers such as urea, ammonium sulfate, ammonium phosphates, potassium salts and the like.

It is recommended that the active ingredients of the present invention be used in admixture with phosphatides to increase their effectiveness on plant diseases. Phosphatides per se are useful fungicides and are derived from the natural source. In this case, a phosphatide selected from the group consisting of soybean lecithin, rapeseed lecithin and egg lecithin is preferably employed.

Examples of the preparation of the invention fungicidal composition for agricultural and horticultural use will now be given. In the Examples the parts are on a weight basis.

PREPARATION EXAMPLE 1

Twenty parts of ferric lactate, 2 parts of white carbon, 2 parts of sodium lignin sulfonate, 4 parts of polyoxyethylene alkyl ether and 72 parts of clay were mixed together and milled to obtain 100 parts of a wettable powder.

PREPARATION EXAMPLE 2

Two parts of oxalic acid and 98 parts of talcum were mixed to obtain 100 parts of dust.

PREPARATION EXAMPLE 3

Twenty parts of aluminum chloride, 10 parts of a mixture of polyoxyethylene alkyl allyl ether and sodium alkylaryl sulfonate, 20 parts of methanol and 50 parts of water were mixed to obtain 100 parts of emulsifiable concentrate.

Next, the effects of preventing various plant disease fungi by use of the agricultural and horticultural fungicidal composition of this invention will be specifically illustrated.

APPLICATION EXAMPLE 1

Test for evaluating the effectiveness of preventing rice blast disease:

Rice stubbles (variety "Jukkoku") were planted in synthetic resin pots of 6 cm in diameter, ten stubbles being planted per pot, and were grown in a greenhouse. The wettable powder prepared in accordance with Preparation Example 1, after dilution with water to a concentration of 2000 ppm, was applied to the rice plant seedlings at the 4-leaf stage at a rate of 50 ml per pot with a sprayer. After the applied solution had dried, spores of rice blast (*Pyricularia oryzae*), which had been cultivated in a chaff culture medium containing powder yeast extract, soluble starch, saccharose and chaff, were suspended in water and sprayed on the rice plant seedlings uniformly. The seedlings so treated were then placed in an inoculation box held at 27°C. and a relative humidity of above 95 % to be infected with the foregoing fungus. Two days after infection, the number of disease lesions per leaf was counted, and the preventive value was calculated as follows:

$$\text{Preventive value (\%)} = \frac{\text{Number of disease lesions of untreated leaf} - \text{Number of disease lesions of treated leaf}}{\text{Number of disease lesions of untreated leaf}} \times 100$$

The results obtained are shown in Table 1 which also shows the results obtained when the rice plant seedlings were inoculated with spores of rice blast by spraying 2 days after application of the test compound solution.

Table 1

| Test compound No. | Concentration applied (ppm) | Preventive value *Two days | Preventive value *Two hours | Phytotoxicity** |
|---|---|---|---|---|
| 1 | 2000 | 70 | 77 | — |
| 2 | ″ | 82 | 90 | — |
| 3 | ″ | 69 | 88 | — |
| 4 | ″ | 82 | 91 | — |
| 5 | ″ | 85 | 88 | — |
| 6 | ″ | 78 | 89 | — |
| 7 | ″ | 62 | 70 | — |
| 8 | ″ | 50 | 77 | — |
| 9 | ″ | 57 | 75 | — |
| 10 | ″ | 83 | 66 | — |
| 11 | ″ | 76 | 66 | — |

Note:
* Nos. of test compounds are corresponding to those of test compounds described already.
** No phytotoxicity was observed.
*** Time until inoculation after treatment.

APPLICATION EXAMPLE 2

Test for evaluating the effectiveness of preventing tobacco mosaic virus and cucumber green mottle mosaic virus. 2-months grown tobacco (variety : xanti) and 2-weeks grown cucumber (variety, Sagami-Hanjiro) were used as test plants in this example. One tree had been planted in 12 cm pot packed with soils sterilized in an autoclave and grown in an air-conditioned greenhouse.

The test plant was placed on a turn-table and was turned while various wettable powders prepared in accordance with Preparation Example 1, which were diluted with water, were applied at a rate of 40 ml per 1 to 3 pots with a spray-gun.

After the applied solution had dried, the test plant was inoculated with tobacco mosaic virus (TMV) or cucumber green mottle virus (water melon strain, CGMMV).

Regarding inoculum, leaves of tobacco infected with TMV or leaves of cucumber infected with CGMMV were mixed with 2 times their weight of distilled water and ground sufficiently in an agate mortar. Thereafter, a large-size contamination was removed by low-speed centrifugation and the turbidity (optical density) of the supernatant solution was adjusted to 0.6 × 10 (260 m$\mu\mu$) by addition of water. The solution was further diluted to 2000 times in the case of TMV whereas it was further diluted to 100 times in the case of CGMMV. After addition of carborundum of 500 mesh size, each of the solutions was applied to the test plant for 0.5 minute with an automatic application equipment. The amount of the applied solution was 1 ml.

After inoculation, the test plants treated were placed in a fungitron held at 25°C. and relative humidity of 60 % to be infected with the foregoing virus. After standing for 7 – 10 days in the case of TMV, and after standing for 10 – 14 days in the case of CGMMV, the extent of infection was examined under illumination of 100 luxes. Each test was repeated two times as twenty — repeated cultivation.

The states of infection were evaluated and given the following ratings:

Extent of infection X = $\frac{\text{Number of stalks not infected}}{\text{Total number of stalks tested}} \times 100$ X = 100 — 90 — A
89 — 75 — B
74 — 50 — C
49 — 35 — D
below 34 — E Table 2

| Test compound | Concentration applied (ppm) | Inhibitory effect against TMV | Inhibitory effect against CUMV | Phytotoxicity |
|---|---|---|---|---|
| 1 | 2000 | B | A | — |
| 2 | " | A | B | — |
| 3 | " | B | A | — |
| 4 | " | A | A | — |
| 5 | " | B | B | — |
| 6 | " | A | B | — |
| 7 | " | A | A | — |
| 8 | " | B | A | — |
| 9 | " | B | B | — |
| 10 | " | C | B | — |
| 11 | " | B | B | — |
| Control | | E | E | |

Table 2-continued

| Test compound (ppm) | Concentration applied | Inhibitory effect against TMV | Inhibitory effect against CUMV | Phytotoxicity |
|---|---|---|---|---|
| (untreated) | | | | |

Note: Nos. of test compounds are corresponding to those of test compounds described already.

The results obtained using CGMMV (cucumber strain) were the same as mentioned above.

APPLICATION EXAMPLE 3

Test for evaluating the effectiveness of preventing citrus melanose.

a. Test plant.

Shoots of about 3-year old seedlings of citrus "Unshu" (2 – 4 trees planted in 6-inch pots)

b. Solution used for test.

The plants were uniformly sprayed with a dilute solution (concentration of compound tested = 2000 ppm) of wettable powder prepared in accordance with the Preparation Example 1, at a rate of 40 ml per two pots.

As control fungicide, "Daisen" (trade name, product of Nihon-Nohyaku Co., Ltd., wettable powder containing zinc ethylene bis (dithiocarbamate) was sprayed at 1000 ppm.

c. Inoculum and method of inoculation.

In preparing a suspension of pycnospores, sterile distilled water was poured on the culture twigs infected with citrus melanose in a test tube. The suspension containing about 200 pycnospores as seen in the field of view of a 150-power microscope was used, and the plants were inoculated by spraying. After completion of the inoculation, the test plants were placed in an inoculation box and held in a humid chamber for 3 days, and after the plants had been thoroughly infected, they were transferred to a greenhouse.

d. Method of inspection.

About 2 – 3 weeks after inoculation, the entire leaves of the shoots were inspected for the development of disease, and the states of infection were evaluated and given the following ratings:

| Number of disease lesions | Rating |
|---|---|
| No spots | 0 |
| 1 – 50 disease lesions | 1 |
| 51 – 150 disease lesions | 2 |
| 151 or more disease lesions | 3 |

The extent of infection and preventive value were then calculated as follows:

Extent of infection = $\frac{1 \times n_1 + 2 \times n_2 + 3 \times n_3}{3 \times N} \times 100$ where $n_1$, $n_2$ and $n_3$ are each the number of leaves whose states of infection were respectively rated as being 1, 2 and 3; and N is the total number of leaves.

Preventive value (%) = $\frac{\text{Extent of infection of untreated leaves} - \text{Extent of infection of treated leaves}}{\text{Extent of infection of untreated leaves}} \times 100$ e. The results of the test are shown in Table 3.

Table 3

| Test compound | Extent of infection | Preventive value (%) | Phytotoxicity |
|---|---|---|---|
| 1 | 13 | 75 | — |
| 2 | 20 | 51 | — |
| 3 | 11 | 79 | — |
| 4 | 13 | 75 | — |
| 5 | 18 | 60 | — |
| 6 | 11 | 79 | — |
| 7 | 20 | 62 | — |
| 8 | 11 | 79 | — |
| 9 | 3 | 95 | — |
| 10 | 1 | 95 | — |
| 11 | 2 | 96 | — |
| "Daisen" | 20 | 62 | — |
| Untreated | 53 | 0 | — |

APPLICATION EXAMPLE 4

Test for evaluating the effectiveness of preventing cucumber anthracnose.

a. Test plant.

2-weeks grown seedlings of cucumber (variety, Sagami-Hanjiro) (2–3 trees planted in 2-inch pot)

b. Solution used for test.

The plants were uniformly sprayed with a dilute solution (concentration of compound tested: 1000 ppm, 2000 ppm) of wettable powder prepared in accordance with the Preparation Example 1, at a rate of 40 ml per two pots, and air-dried.

Also, the test compounds were mixed with soybean lecithin in an equal amount and each of the mixtures was diluted with water and sprayed at 1000 ppm concentration of test compound and 1000 ppm concentration of soybean lecithin.

As control fungicide Daisen was sprayed.

c. Inoculum and method of inoculation.

Spores of cucumber *colletotrichum lagenarium* cultured on the agar slant (sweet corn extract solution containing 1 % sucrose) for 1 week at 22°C. was suspended in water. The suspension containing 120 spores as seen in the field of view of a 150-power microscope was applied on the test plants at a rate of 40 ml per two pots. Thereafter, the test plants were placed in a fungitron of 22°C. and relative humidity of above 90 % for 1 day to be infected thoroughly and then they were placed in a greenhouse for 4 days.

d. Method of inspection.

The number of disease lesions that appeared on the leaves was counted. The inspection was conducted by counting the number of disease lesions per two leaves and the number of disease lesions of four leaves per pot.

$$\text{Preventive value (\%)} = \frac{\text{Number of disease lesions of untreated leaf} - \text{Number of disease lesions of treated leaf}}{\text{Number of disease lesions of untreated leaf}} \times 100$$

The results this test are shown in Tables 4 and 5.

Table 4

| Test compound | Concentration applied (ppm) | Preventive value (%) | Phytotoxicity |
|---|---|---|---|
| 1 | 1000 | 42 | — |
|  | 2000 | 75 | — |
| 2 | 1000 | 52 | — |
|  | 2000 | 90 | — |
| 3 | 1000 | 49 | — |
|  | 2000 | 69 | — |
| 4 | 1000 | 51 | — |
|  | 2000 | 84 | — |
| 5 | 1000 | 43 | — |
|  | 2000 | 75 | — |
| 6 | 1000 | 61 | — |
|  | 2000 | 85 | — |
| 7 | 1000 | 55 | — |
|  | 2000 | 91 | — |
| 8 | 1000 | 50 | — |
|  | 2000 | 80 | — |
| 9 | 1000 | 49 | — |
|  | 2000 | 85 | — |
| 10 | 1000 | 47 | — |
|  | 2000 | 89 | — |
| 11 | 1000 | 41 | — |
|  | 2000 | 95 | — |
| Soybean lecithin | 1000 | 74 | — |
|  | 2000 | 95 | — |
| "Daisen" | 1000 | 92 | — |
| Untreated | — | — |  |

Table 5

| Test compound | Concentration applied | Preventive value (%) |
|---|---|---|
| Soybean lecithin + 1 | 1000 ppm + 1000 ppm | 93 |
| Soybean lecithin + 2 | 1000 ppm + 1000 ppm | 85 |
| Soybean lecithin + 3 | 1000 ppm + 1000 ppm | 73 |
| Soybean lecithin + 4 | 1000 ppm + 1000 ppm | 85 |
| Soybean lecithin + 5 | 1000 ppm + 1000 ppm | 75 |
| Soybean lecithin + 6 | 1000 ppm + 1000 ppm | 86 |
| Soybean lecithin + 7 | 1000 ppm + 1000 ppm | 95 |
| Soybean lecithin + 8 | 1000 ppm + 1000 ppm | 91 |
| Soybean lecithin + 9 | 1000 ppm + 1000 ppm | 93 |
| Soybean lecithin + 10 | 1000 ppm + 1000 ppm | 91 |
| Soybean lecithin + 11 | 1000 ppm + 1000 ppm | 85 |

What is claimed is:

1. A fungicidal composition containing as an active ingredient, sucrose fatty acid ester whose ester group is derived from a fatty acid having 8 to 18 carbon atoms in an amount of about 0.1–90% by weight, based on the weight of the composition, and at least on adjuvant selected from the group consisting of solid carrier, liquid carrier, emulsifying agent, dispersing agent and surface active agent.

2. The fungicidal composition of claim 1 wherein said active ingredient is combined with a phosphatide derived from a natural source, wherein the phosphatide is selected from the group consisting of soy bean lecithin, rapeseed lecithin and egg lecithin.

3. A method for protecting agricultural plants selected from fruit-bearing plants, berry-bearing plants, vegetables and tobacco plants from attack by plant disease causative organisms of rice blast, bacterial leaf blight, citrus canker, citrus melanose, cucumber anthracnose, cucumber phyrophthora rot, cucumber powdery mildew, cucumber downy mildew, tomato leaf mold, tomato leaf blight, tomato leaf spot, tobacco mosaic and cucumber green mottle mosaic, which comprises applying to said agricultural plant from about 10 grams per 10 ares to 2000 grams per 10 ares of an active ingredient selected from sucrose fatty acid ester whose ester groups are derived from a fatty acid having 8 to 18 carbon atom.

4. The method of claim 3 wherein said active ingredient is combined with a phosphatide derived from a natural source selected from the group consisting of soy bean lecithin, rapeseed lecithin and egg lecithin.

5. The method of claim 3 wherein said fatty acid is selected from the group consisting of caprylic acid, lauric acid, palmitic acid and myristic acid.

6. The method of claim 3 wherein said active ingredient is sugar laurate.

7. The method of claim 3 wherein said active ingredient is sugar myristate.

8. The method of claim 3, wherein said agricultural plant is selected from the group consisting of tobacco, citrus, persimmon, apple, pear, peach, plum, apricot, cherry, loquat, grape, fig, pineapple, banana, strawberry, olive, tomato, eggplant, pepper, cucumber, melons, watermelon, pumpkin, radish, cabbage, cauliflower, turnip, onion, asparagus, lettuce, carrot, celery, spinach, dasheen, ginger, pea, potato, beans, rice, barley and wheat.

9. The method of claim 3 for protecting rice plants from rice blast disease.

10. The method of claim 3 for protecting tobacco plants from tobacco mosaic virus.

11. The method of claim 3 for protecting cucumber plants from cucumber green mottle mosaic virus.

12. The method of claim 3 for protecting citrus plants from citrus melanose.

13. The method of claim 3 for protecting cucumber plants from cucumber anthracnose.

14. The method of claim 4, wherein said agricultural plant is selected from the group consisting of tobacco, citrus, persimmon, apple, pear, peach, plum, apricot, cherry, loquat, grape, fig, pineapple, banana, strawberry, olive, tomato, eggplant, pepper, cucumber, melons, watermelon, pumpkin, radish, cabbage, cauliflower, turnip, onion, asparagus, lettuce, carrot, celery, spinach, dasheen, ginger, pea, potato, beans, rice, barley, wheat, etc.

15. The method of claim 4 for protecting rice plants from rice blast disease.

16. The method of claim 4 for protecting tobacco plants from tobacco mosaic virus.

17. The method of claim 4 for protecting cucumber plants from cucumber green mottle mosaic virus.

18. The method of claim 4 for protecting citrus plants from citrus melanose.

19. The method of claim 4 for protecting cucumber plants from cucumber anthracnose.

20. The method of claim 4, wherein said fatty acid is caprylic acid, lauric acid, palmitic acid or myristic acid.

21. The fungicidal composition of claim 1, wherein said fatty acid is caprylic acid, lauric acid, palmitic acid or myristic acid.

22. The fungicidal composition of claim 2, wherein said fatty acid is caprylic acid, lauric acid, palmitic acid or myristic acid.

* * * * *